United States Patent [19]

Skotnicki et al.

[11] Patent Number: 4,748,246
[45] Date of Patent: May 31, 1988

[54] PYRAZOLO(4,3-C)QUINOLINES

[75] Inventors: Jerauld S. Skotnicki, Chadds Ford; Steven C. Gilman, Newtown Square; Bruce A. Steinbaugh, King of Prussia; John H. Musser, Malvern, all of Pa.

[73] Assignee: American Home Products Corporation, New York, N.Y.

[21] Appl. No.: 47,969

[22] Filed: May 7, 1987

[51] Int. Cl.$^4$ .................................. C07D 471/04
[52] U.S. Cl. ................... 544/331; 544/238; 544/284; 544/316; 544/333; 544/353; 544/354; 544/355; 544/356; 544/405; 546/82
[58] Field of Search ............. 546/82; 544/316, 331, 544/333, 238, 353, 354, 355, 356, 284, 405

[56] References Cited
PUBLICATIONS

Sangwan, N., et al., *Indian Journal of Chemistry*, 24B, 639–644 (1985).

*Chemical Abstracts*, 88:99030m (1978), [NASR, M. et al., *J. Med. Chem.* 1978, 21, (3), 295–8].

*Primary Examiner*—Richard A. Schwartz
*Attorney, Agent, or Firm*—George Tarnowski

[57] ABSTRACT

There are disclosed compounds of the formula

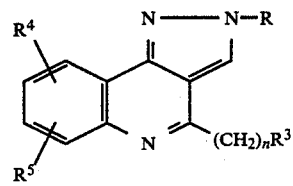

wherein the various substituents are defined hereinbelow, and, by virtue of their ability to inhibit interleukin 1, their use as antiinflammatory agents and in treatment of disease states involving enzymatic tissue destruction.

14 Claims, No Drawings

PYRAZOLO(4,3-C)QUINOLINES

This invention relates to novel compounds possessing interleukin 1 (IL 1) antagonist activity and having antiinflammatory activity.

Interleukin 1 (IL 1) is a peptide hormone exhibiting a number of immune and inflammatory actions [Dinarello, *Rev. Inf. Dis.* 6, 51 (1984)]. IL 1 is produced, in response to inflammatory stimuli, by leukocytes such as macrophages and polymorphonuclear cells, as well as by a variety of other cell types such as synovial cells, endothelial cells and keratinocytes, and it mediates several biological responses of leukocytes on other tissue targets such as bone, articular joints, liver, hypothalamus, and brain.

IL 1 was originally shown to augment the proliferation of T lymphocytes for which it was named lymphocyte activating factor (LAF), and is believed to be important for the generation of T cell-dependent immune responses.

There is evidence to suggest a relationship between IL 1 and pathology in various diseases, particularly immunoinflammatory disorders such as rheumatoid arthritis [Dinarello et al., *Ann. Rev. Med.* 37, 173 (1986)]. IL 1 induces acute inflammatory responses producing soft tissue swelling (edema and erythema) [Grandstein et al., *J. Clin. Invest.*, 77, 1010 (1986)]. It is a chemoattractant for polymorphonuclear leukocytes (PMN) and induces the activation and migration of these cells into tissues. IL 1 also stimultates the production of prostaglandin $E_2$, a potent inflammatory arachidonic acid metabolite, by a variety of cells and tissues including chondrocytes and synovial cells [Mizel et al., *Proc. Nat'l. Acad. Sci.*, 78, 2474 (1981) and Chang et al., *J. Immunol.*, 136, 1283 (1986)] and hypothalamic tissue. This effect on the hypothalamus is thought to be responsible for fever production. IL 1 can induce articular joint destruction by stimulating the production of a variety of hydrolytic enzymes (neutral proteases such as collagenase, glycosaminoglycanases, etc.) which degrade cartilage matrix proteins (collagen, proteoglycan, etc.) by synovial cells, chondrocytes, and fibroblasts [Dayer et al., *Science*, 195, 181 (1977) and Postlethwaite et al., *J. Exp. Med.*, 157, 801 (1983)]. Furthermore, IL 1 induces hyperproliferation of dermal and synovial fibroblasts and is a potent inducer of bone resorption [Wood et al., *J. Immunol.*, 134, 895 (1985) and Gilman and Kimball, *Agents and Actions*, 16, 468 (1985)].

Finally, IL 1 mediates acute phase reactions including alterations in plasma divalent cations, increased synthesis by liver cells of acute phase proteins (C-reactive protein, serum amyloid A, etc.) and fever. Accordingly, compounds which have IL 1 antagonist activity and thereby inhibit the biological effects of IL 1 can be advantageously used to block pathologies in which one or more of these events occur such as rheumatoid arthritis, osteoarthritis and related disorders [Rodnan and Schumacher, eds, "Primer on the Arthritic Diseases" 8 ed. Atlalnta, 1983], psoriasis and other inflammatory/proliferative skin disorders as well as diseases in which the secretion of collagenase (and other tissue hydrolysing neutral proteinases) has been implicated as a causative factor, including periodontal disease, tumor invasiveness, and epidermolysis bullosa [Perez-Tamayo, *Amer. J. Pathol.*, 92, 509 (1978) and Harris and Krane, *N. Engl. J. Med.*, 291, 652 (1974)] and so forth.

It has now been found that certain novel substituted pyrazolo [4,3-c] quinolines antagonize the activity of IL 1, and so are useful as antiinflammatory agents and in the treatment of pathologies whose etiology is collagenase-based tissue destruction. The present invention provides novel compounds having the formula:

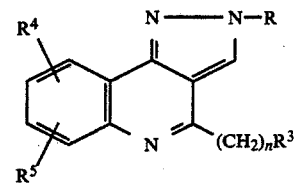

wherein

R is lower alkyl, carboxy lower alkyl, alkoxy carbonyl lower alkyl, cyano lower alkyl, nitro lower alkyl, hydroxy lower alkyl, lower alkoxy lower alkyl, $COR^1$, $CO_2R^2$, $CON(R^2)_2$, $SO_2R^1$, phenyl, naphthyl, pyridyl, quinolinyl or phenyl, naphthyl, pyridyl or quinolinyl substituted by halo, lower alkyl, lower alkoxy, nitro, cyano, amino, mono-lower alkyl amino, di-lower alkyl amino, carboxy, lower alkoxycarbonyl or hydroxy;

$R^1$ is phenyl, phenyl lower alkyl, naphthyl, pyridyl, quinolinyl, pyrazinyl, pyridinyl, pyrimidinyl, pyridazinyl, quinoxalinyl, quinazolinyl or any of the foregoing substituted with halo, lower alkyl, carboxy, cyano, nitro, lower alkylsulfonyl, lower alkoxy carbonyl or lower alkyl substituted by fluoro, carboxy, cyano, nitro or lower alkoxy carbonyl;

$R^2$ is hydrogen, lower alkyl, phenyl or benzyl;

$R^3$ is hydrogen, $R^1$, $OR^1$, $SR^1$, $NR^2R^1$, $NH_2$, $NR^6R^1$ or $NR^6R^7$;

$R^4$ and $R^5$ are each independently, hydrogen, halo, lower alkoxy, lower alkyl, trifluoromethyl, cyano, nitro, carboxy or lower alkoxycarbonyl;

$R^6$ is carbamoyl, phenylcarbamoyl, or halophenylcarbamoyl;

$R^7$ is hydrogen or lower alkyl; and n is 1-5.

The terms "lower alkyl" and "lower alkoxy" refer to moieties having 1 to 6 carbon atoms in the carbon chain. The term "halo" refers to fluoro, chloro and bromo.

The especially preferred compounds are those having the formula

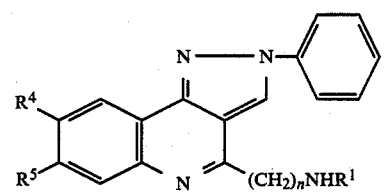

wherein $R^1$ is substituted phenyl, in particular halo-, cyano-, lower alkylsulfonyl or lower alkyl carbonyl-substituted phenyl, pyrimidinyl, pyrazinyl or quinolinyl;

$R^4$ is hydrogen, $R^3$ is halo and n is 2-3.

The compounds of the invention can be prepared by several routes. According to one route, 1,4-dioxa-8-azaspiro[4.5]decane is reacted with a suitable halo-$R^1$ reactant, and following ketal hydrolysis, the resultant intermediate is reacted with a suitably substituted amino benzoic acid in the presence of a halogenating agent to yield an intermediate halogenated benzo[b][1,6]naphthyridine:

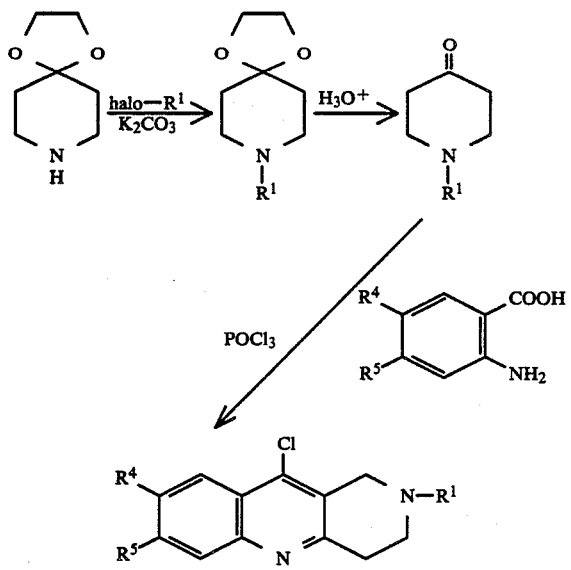

In the final step, the intermediate halogenated benzo[b][1,6]naphthyridine is reacted with a suitably substituted hydrazine to yield the desired final product:

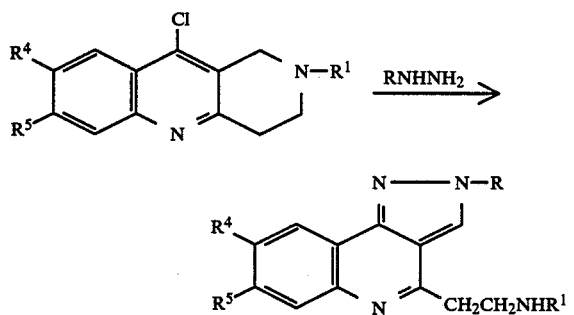

Compounds having $R^3$ substituents other than aryl can be prepared therefrom by the following representative reaction:

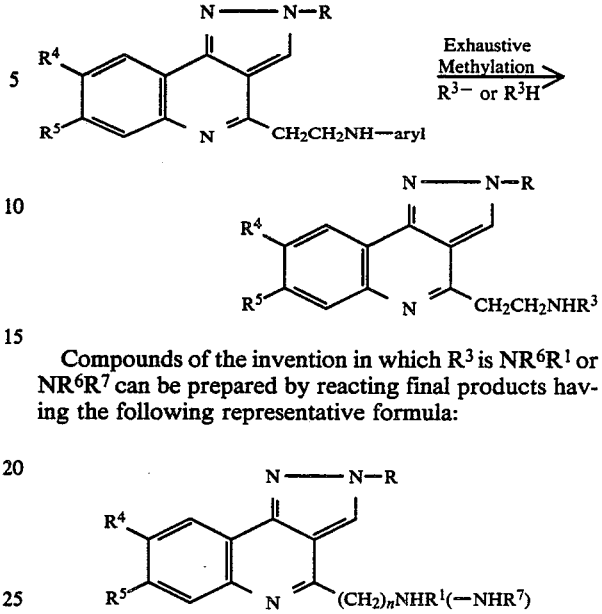

Compounds of the invention in which $R^3$ is $NR^6R^1$ or $NR^6R^7$ can be prepared by reacting final products having the following representative formula:

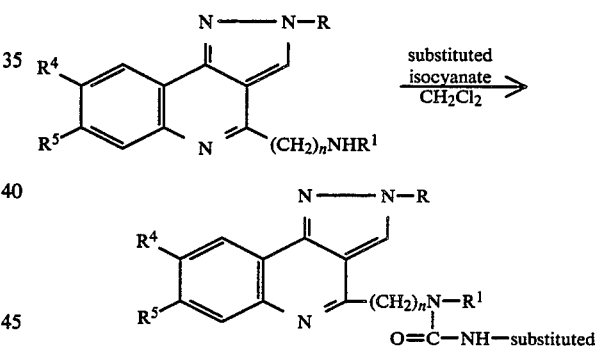

with an appropriately substituted $R^6$-bearing reactant. For example, where $R^6$ is a carbamoyl containing moiety, this reaction can be carried out using an appropriate substituted isocyanate in the presence of methylene chloride:

In another preparation scheme, a suitably substituted aniline is reacted with an appropriate acrylic acid ester derivative or a protected alcohol thereof, followed by protection of the ring nitrogen of the resulting dihydronaphthyridinone:

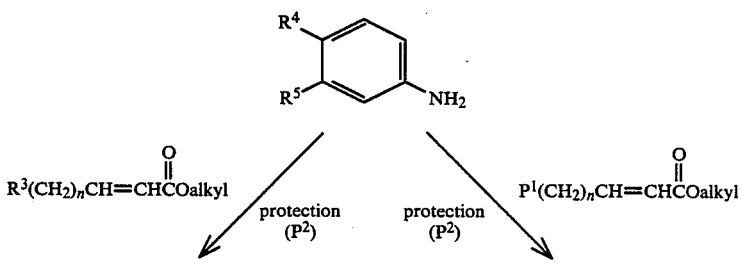

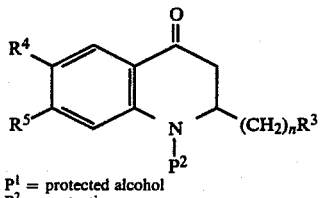
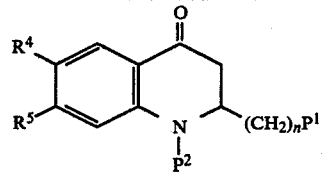

P¹ = protected alcohol
P² = protecting group

The resulting dihydronaphthyridiones are treated with ethyl formate followed by reaction with a suitably substituted hydrazine, deprotection of the ring nitrogen and finally oxidation:

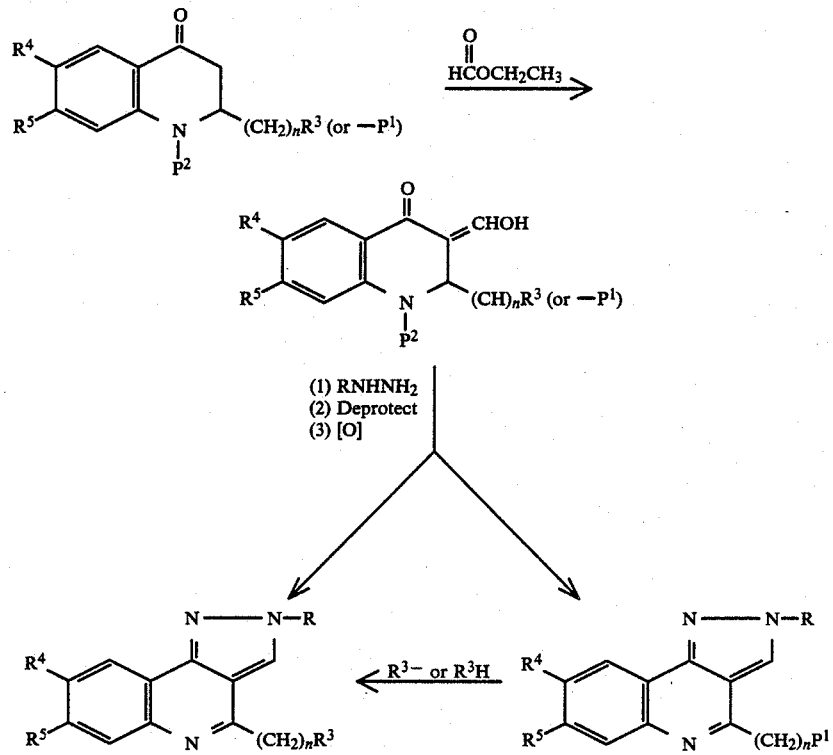

In the above sequence, the P¹ protecting group is transformed into a suitable leaving group and the intermediate is then reacted so as to replace the leaving group with the desired R³ group to yield the desired final product.

The starting materials used in the above outlined preparative sequences are all available commercially or can be prepared by conventional methods disclosed in the chemical literature.

The compounds of the invention, by virtue of the ability to antagonize interleukin 1, are useful in the treatment of such diseases as rheumatoid arthritis, osteoarthritis, tendinitis, bursitis and similar conditions involving inflammation, as well as psoriasis and other inflammatory/proliferative skin disorders. Moreover, the compounds are useful in treating disease states involving enzymatic tissue destruction, for example, conditions in which collagenase has been implicated as a causative factor, such as rheumatoid arthritis joint destruction, periodontal disease, tumor invasiveness, corneal ulcerations, epidermolysis bullosa and the like.

When the compounds of the invention are employed as antiinflammatory agents, or collagenase inhibitors, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For topical administration, the compounds may be formulated in the form of dusting powders, solutions, creams, lotions or aerosols in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, of if desired, the dosage may be divided into convenient subunits administered at suitable times throughout the day.

The interleukin 1 antagonist activity, as well as the antiinflammatory effects of the compounds of the invention may be demonstrated by standard pharmacological procedures, which are described more fully in the examples given hereinafter.

These procedures illustrate the ability of the compounds of the invention to inhibit the IL 1-induced release of neutral protease from articular chondrocytes; and measure the in vivo antiinflammatory activity of the compounds in the rat carageenan paw edema assay.

The following examples show the preparation and pharmacological testing of compounds within the invention.

EXAMPLE 1

4-[[2-(7-Chloro-2-phenyl-2H-pyrazolo-[4,3-c]quinolin-4-yl)ethyl]amino]benzonitrile A. 4-(1,4-Dioxa-8-azaspiro[4.5]dec-8-yl)benzonitrile A mixture of 10 g (0.0825 mol) p-fluorobenzonitrile, 47 g (0.3282 mol) of 1,4-dioxa-8-azaspiro[4.5]decane, 17 g (0.123 mol) of $K_2CO_3$, and 100 ml of acetonitrile is stirred at 90°-100° C. for three days. The reaction mixture is allowed to cool to ambient temperature, diluted with water and extracted with methylene chloride. The combined extracts are washed with brine, dried over $Na_2SO_4$, and concentrated in vacuo to give a pasty solid. Trituration with ether furnishes 13.4 g (67%) of title compound: IR (KBr) 2210 and 1600 cm$^{-1}$; NMR (CDCl$_3$) δ 7.48 (d, 2H), 6.88 (d, 2H), 4.0 (s, 4H), 3.58–3.40 (m, 4H), and 1.90–1.70 (m, 4H).

B. 4-(4-Oxo-1-piperidinyl)benzonitrile

A mixture of 12 g (0.049 mol) of the ketal of step A. above, 120 ml of 10% sulfuric acid solution, and 60 ml of tetrahydrofuran is stirred at ambient temperature for 4 days. The reaction mixture is diluted with water and extracted with methylene chloride. The combined organic extracts are dried over $Na_2SO_4$ and concentrated in vacuo to give a pasty solid. Trituration with ether provides 4.6 g (46%) of title compound: IR (KBr) 2220 and 1700 cm$^{-1}$; NMR (CDCl$_3$) δ 7.54 (d, 2H), 6.90 (d, 2H), 3.88–3.66 (m, 4H), and 2.70–2.52 (m, 4H).

C.

4-(7,10-Dichloro-3,4-dihydrobenzo[b][1,6]naphthyridin-2(1H)-yl)benzonitrile

To a slurry of 14.567 g (0.0849 mol) of 2-amino-4-chlorobenzoic acid and 71.22 ml of phosphorous oxychloride is added portionwise 17 g (0.0849 mol) of the compound of step B. above. The mixture is stirred under reflux for 3 hours and concentrated in vacuo. The residue is taken up in chloroform and poured carefully into a mixture of ice-NH$_4$OH and stirred for 30 min. before extraction with chloroform. The combined extracts are washed with brine, dried over $Na_2SO_4$, and concentrated in vacuo to yield 26.48 g of solid. Purification by HPLC and trituration with ether furnishes 2.285 g (8%) of title compound as a yellow-orange solid: m.p. 209°–211° C.; IR (KBr) 3430, 2210, and 1604 cm$^{-1}$; NMR (CDCl$_3$) 8.19 (d, 1H), 8.08 (s, 1H), 7.61 (m, 3H), 7.03 (d, 2H), 4.75 (s, 2H), 3,87 (t, 2H), 3.57 (t, 2H).

Analysis for: $C_{19}H_{13}Cl_2N_3$. Calculated: C, 64.42; H, 3.70; N, 11.86. Found: C, 64.07; H, 3.69; N, 11.68.

D.

4[[2-(7-Chloro-2-phenyl-2H-pyrazolo[4,3-c]quinolin-4-yl)ethyl]amino]benzonitrile A mixture of 1 g (2.82 mmol) of the compound of step C. above, 0.611 ml (6.21 mmol) of phenylhydrazine, 0.75 ml of conc. hydrochloric acid, and 30 ml of absolute ethanol is stirred under reflux for 6 hours. The cooled precipitate is dissolved in methanol and treated with a $Na_2CO_3$ solution. The precipitate which forms is collected and washed with water to yield 0.625 g of tan solid. Recrystallization from acetonitrile affords 0.252 g (21%) of title compound as a yellow solid: m.p. 208°–211° C.; IR (KBr 3324, 2200, and 1600 cm$^{-1}$; NMR (DMSO-d$_6$) δ 9.58 (s, 1H), 8.46 (d, 1H), 8.18 (d, 2H), 8.06 (s, 1H), 7.69 (m, 3H), 7.52 (m, 3H), 6.88 (m, 1H), 6.75 (d, 2H), 3.79 (m, 2H), 3.45 (t, 2H).

Analysis for: $C_{25}H_{18}ClN_5$. Calculated: C, 70.83; H, 4.28; N, 16.52. Found: C, 70.38; H, 4,42; N, 16.70.

EXAMPLE 2

4-[[2-(7-Chloro-2-phenyl-2H-pyrazolo[4,3-c]quinolin-4-yl)ethyl]amino]benzoic acid ethyl ester A. 4-(1,4-Dioxa-8-azaspiro[4.5]dec-8-yl)benzoic acid ethyl ester A mixture of 50 g (0.349 mol) of ethyl p-fluorobenzoate, 185 g (1.29 mol) of 1,4-dioxa-8-azaspiro[4.5]decane, 73 g (0.5282 mol) of $K_2CO_3$, and 400 ml of acetonitrile is stirred at 90°-100° C. for three days. The reaction mixture is allowed to cool to ambient temperature, diluted with water, and extracted with methylene chloride. The combined organic extracts are washed with brine, dried over $Na_2SO_4$, and concentrated in vacuo to give a pasty solid. Trituration with ether furnishes 31 g (23%) of title compound: IR (KBr) 1695 and 1610 cm$^{-1}$; NMR (CDCl$_3$) δ 7.98 (d, 2H), 6.96 (m, 2H), 4.36 (q, 2H), 4.02 (s, 4H), 3.58–3.48 (m, 4H), 1.92–1.80 (m, 4H), and 1.38 (t, 3H).

B. 4-(4-Oxo-1-piperidinyl)benzoic acid ethyl ester

A mixture of 2.7 g (0.0093 mol) of the ketal of step A. above, 30 ml of 10% sulfuric acid solution, and 15 ml of tetrahydrofuran is stirred at ambient temperature for 4 days. The reaction mixture is diluted with water and extracted with methylene chloride. The combined organic extracts are dried over $Na_2SO_4$ and concentrated in vacuo to give 1.2 g (52%) of title compound: IR (KBr) 1725 and 1695 cm$^{-1}$; NMR (CDCl$_3$) δ 8.04 (d, 2H), 7.96 (d, 2H), 4.38 (q, 2H), 3.98 (t, 4H), 2.6 (t, 4H), and 1.38 (t, 3H).

C.

4-(7,10-Dichloro-3,4-dihydrobenzo[b][1,6]naphthyridin-2(1H)-yl)benzoic acid ethyl ester To a slurry of 12.212 g (0.0712 mol) of 2-amino-4-chlorobenzoic acid and 60 ml of phosphorous oxychloride is added portionwise 17.6 (0.0712 mol) of the compound of step B. above. The mixture is stirred under reflux for 2½ hrs. and then concentrated in vacuo. The residue is taken up in chloroform and slowly added to an ice-NH$_4$OH mixture. The mixture is stirred for 30 min. and then extracted with chloroform. The combined extracts are washed with brine, dried over Na$_2$SO$_4$, and concentrated in vacuo to yield 38.59 g of solid. Purification by HPLC furnishes 2.29 g (8%) of title compound as an orange solid: m.p. 155°–158° C. (dec.); IR (KBr) 1705, 1608, and 1282 cm$^{-1}$; NMR (CDCl$_3$) δ 8.20 (d, 1H), 8.05 (m, 3H), 7.59 (m, 1H), 7.04 (d, 2H), 4.76 (s, 2H), 4.37 (q, 2H), 3.88 (t, 2H), 3.37 (t, 2H), 1.38 (t, 3H).

Analysis for: C$_{21}$H$_{18}$Cl$_2$N$_2$O$_2$. Calculated: C, 62.85; H, 4.52; N, 6.98. Found: C, 62.52; H, 4.48; N, 6.98.

D.
4-[[2-(7-Chloro-2-phenyl-2H-pyrazolo[4,3-c]quinolin-4-yl)ethyl]amino]benzoic acid ethyl ester A mixture of 1 g (2.5 mmol) of the compound of step C. above, 0.539 ml (5.48 mmol) of phenylhydrazine, 0.75 ml of conc. hydrochloric acid, and 30 ml of absolute ethanol is stirred under reflux for 6 hrs. The cooled precipitate is dissolved in methanol and treated with a Na$_2$CO$_3$ solution. The precipitate is collected and washed with water to yield 0.388 of a brown solid. Trituration with ether affords 0.303 g (26%) of the title compound as a light brown solid: m.p. 170°–172° C.; IR (KBr) 3320, 1687, and 1604 cm$^{-1}$; NMR (DMSO-d$_6$) δ 9.56 (s, 1H), 8.27 (d, 1H), 8.17 (d, 2H), 8.07 (s, 1H), 7.70 (m, 5H), 7.54 (t, 1H), 6.70 (d, 2H), 4.23 (q, 2H), 3.78 (m, 2H), 3.46 (t, 2H), 1.26 (t, 3H).

Analysis for: C$_{27}$H$_{23}$ClN$_4$O$_2$. Calculated: C, 68.86; H, 4.92; N, 11.90. Found: C, 68.21; H, 4.94; N, 11.75.

EXAMPLE 3

7-Chloro-2-phenyl-N-(2-pyrimidinyl)-2H-pyrazolo[4,3-c]quinoline-4-ethanamine

A. 8-(2-Pyrimidinyl)-1,4-dioxa-8-azaspiro[4.5]decane

A mixture of 10 g (0.0873 mol) of 2-chloropyrimidine, 38 g (0.2654 mol) of 1,4-dioxa-8-azaspiro[4.5]decane, 18 g (0.130 mol) of K$_2$CO$_3$, and 100 ml of dimethylformamide is stirred at 100°–110° C. for 4 days. The reaction mixture is allowed to cool to ambient temperature, diluted with water and extracted with ethyl acetate. The combined organic extracts are washed copiously with water, then brine, dried over Na$_2$SO$_4$, and concentrated in vacuo to give a waxy solid. Trituration with ether furnishes 8.25 g (48%) of title compound: IR (KBr) 1670 and 1585 cm$^{-1}$; NMR (CDCl$_3$) δ 8.30 (t, 1H), 6.46 (d, 2H), 4.02 (s, 4H), 3.98–3.88 (m, 4H), and 1.90–1.66 (m, 4H).

B. 1-(2-Pyrimidinyl)-4-piperidinone

A mixture of 8 g (0.036 mol) of the ketal of step A. above, 80 ml of 10% sulfuric acid solution, and 40 ml of tetrahydrofuran is stirred at ambient temperature for 3 days. The reaction mixture is diluted with water, basified with 2N sodium hydroxide solution and extracted with methylene chloride. The combined organic extracts are dried over Na$_2$SO$_4$ and concentrated in vacuo to give a waxy solid. Trituration with ether affords 2.9 g (45%) of title compound: IR (KBr) 1710 and 1585 cm$^{-1}$; NMR (CDCl$_3$) δ 8.36 (d, 1H), 7.6 (t, 2H), 4.30–4.08 (m, 4H), and 2.62–2.46 (m, 4H).

C.
7,10-Dichloro-1,2,3,4-tetrahydro-2-(2-pyrimidinyl)benzo[b][1,6]naphthyridine

To a slurry of 16.75 g (0.0976 mol) of 2-amino-4-chlorobenzoic acid and 81.88 ml of phosphorous oxychloride is added portionwise 17.3 g (0.0976 mol) of the compound of step B. The mixture is stirred under reflux for 3 hrs. and then concentrated in vacuo. The residue is dissolved in chloroform and slowly added to an ice-NH$_4$OH mixture. The mixture is stirred for 30 min. and extracted with chloroform. The combined extracts are washed with brine, dried over Na$_2$SO$_4$, and concentrated in vacuo to yield 32.49 g of solid. Purification by HPLC and recrystallization from benzene furnishes 2.26 g (7%) of title compound as a pink solid: m.p. 172°–174° C.; IR (KBr) 1587 and 1465 cm$^{-1}$; NMR (CDCl$_3$) δ 8.46 (d, 2H), 8.19 (d, 1H), 8.07 (s, 1H), 7.58 (m, 1H), 6.62 (t, 1H), 5.22 (s, 2H), 4.29 (t, 2H), 3.31 (t, 2H).

Analysis for: C$_{16}$H$_{12}$Cl$_2$N$_4$. Calculated: C, 58.02; H, 3.65; N, 16.92. Found: C, 58.05; H, 3.72; N, 16.70.

D.
7-Chloro-2-phenyl-N-(2-pyrimidinyl)-2H-pyrazolo[4,3-c]quinoline-4-ethanamine

A mixture of 1 g (3.02 mmol) of the compound of step C. above, 0.654 ml (6.64 mmol) of phenylhydrazine, 0.75 ml of conc. hydrochloric acid, and 30 ml. of absolute ethanol is stirred under reflux for 6 hrs. The cooled precipitate is dissolved in methanol and treated with a Na$_2$CO$_3$ solution. The precipitate is collected and washed with water to yield an off-white solid. Recrystallization from benzene affords 0.441 g of an off-white solid. Purification by HPLC followed by trituration with methylene chloride affords 0.088 g (7%) of title compound as a tan solid: m.p. 213°–215° C.; IR (KBr) 3280, 1585, and 1525 cm$^{-1}$; NMR (DMSO-d$_6$) δ 9.55 (s, 1H), 8.47 (d, 1H), 8.31 (d, 2H), 8.18 (d, 2H), 8.06 (s, 1H), 7.70 (m, 3H), 7.55 (t, 1H), 7.29 (t, 1H), 6.60 (t, 1H), 3.92 (m, 2H), 3.4 (t, 2H).

Analysis for: C$_{22}$H$_{17}$ClN$_6$. Calculated: C, 65.91; N, 4.28; N, 20.97. Found: C, 65.62; H, 4.44; N, 21.38.

EXAMPLE 4

7-Chloro-2-phenyl-N-(2-quinolinyl)-2H-pyrazolo[4,3-c]quinoline-4-ethanamine

A. 8-(2-Quinolinyl)-1,4-dioxa-8-azaspiro[4.5]decane

A mixture of 10 g (0.0613) of 2-chloroquinoline, 27 g (0.1886 mol) of 1,4-dioxa-8-azaspiro[4.5]decane, 13 g (0.0941) of K$_2$CO$_3$, and 75 ml of dimethylformamide is stirred at 100°–110° C. for 4 days. The reaction mixture is allowed to cool to ambient temperature, diluted with water and extracted with ethyl acetate. The combined organic extracts are washed copiously with water, then brine, dried over Na$_2$SO$_4$, and concentrated in vacuo to give a waxy solid. Trituration with ether furnishes 3.6 g (22%) of title compound: IR (KBr) 1620, 1610, and 1510 cm$^{-1}$; NMR (CDCl$_3$) δ 7.92 (d, 1H), 7.78–7.50 (m, 3H), 7.30–7.22 (m, 1H), 7.04 (d, 1H), 4.02 (s, 4H), 3.94–3.86 (m, 4H), and 1.88–1.76 (m, 4H).

B. 1-(2-Quinolinyl)-4-piperidinone

A mixture of 3 g (0.011 mol) of the ketal of step A. above, 30 ml of 10% sulfuric acid solution, and 15 ml of tetrahydrofuran is stirred at ambient temperature for 4 days. The reaction mixture is diluted with water, basified using 2N sodium hydroxide solution, and extracted with methylene chloride. The combined organic extracts are dried over Na$_2$SO$_4$, and concentrated in vacuo to give a waxy solid. Trituration with ether furnishes 1.3 g (52%) of title compound: IR (KBr) 1710, 1610, and 1600 cm$^{-1}$; NMR (CDCl$_3$) δ 7.96 (d, 1H), 7.80–7.18 (m, 4H), 7.04 (d, 1H), 4.16–4.02 (m, 4H), and 2.66–2.50 (m, 4H).

C. 7,10-Dichloro-1,2,3,4-tetrahydro-2-(2-quinolinyl)benzo[b][1,6]naphthyridine To a slurry of 9.1 g (0.053 mol) of 2-amino-4-chlorobenzoic acid and 45 ml of phosphorous oxychloride is added portionwise 12 g (0.053 mol) of the compound of step B. above. The mixture is stirred under reflux for 2½ hrs. and then concentrated in vacuo. The residue is taken up in chloroform and slowly added to an ice-NH$_4$OH mixture. The mixture is stirred for 30 min. before being extracted with chloroform. The combined extracts are washed with brine, dried over Na$_2$SO$_4$, and concentrated in vacuo to yield 24.55 g of a solid. Purification by HPLC and recrystallization from benzene affords 6.65 g (33%) of title compound as an off-white solid: m.p. 160°–162° C.; IR (KBr) 1602 and 1508 cm$^{-1}$; NMR (CDCl$_3$) δ 8.19 (d, 1H), 8.03 (m, 2H), 7.84 (br, 1H), 7.62 (m, 3H), 7.30 (m, 1H), 7.17 (d, 1H), 5.18 (s, 2H), 4.22 (t, 2H), 3.36 (t, 2H).

Analysis for: C$_{21}$H$_{15}$Cl$_2$N$_3$. Calculated: C, 66.33; H, 3.98; N, 11.05. Found: C, 66.72; H, 4.02; N, 10.86.

D. 7-Chloro-2-phenyl-N-(2-quinolinyl)-2H-pyrazolo[4,3-c]quinoline-4-ethanamine A mixture of 1 g (2.63 mmol) of the compound of step C. above, 0.569 ml (5.79 mmol) of phenylhydrazine, 0.75 ml of conc. hydrochloric acid and 30 ml of absolute ethanol is stirred under reflux for 6 hrs. The precipitate on cooling is collected and dissolved in methanol. Treatment with a Na$_2$CO$_3$ solution results in a precipitate which is filtered and washed with water to furnish a purple-brown solid. Recrystallization from benzene affords 0.367 g as an off-white solid. Purification by HPLC yields 0.210 g (18%) of title compound as a yellow-white solid: m.p. 205°–208° C. (dec.); IR (KBr) 3290, 1620, and 1530 cm$^{-1}$; NMR (DMSO-d$_6$) δ 9.53 (s, 1H), 8.46 (d, 1H), 8.10 (m, 3H), 7.86 (d, 1H), 7.66 (m, 4H), 7.53 (m, 3H), 7.20 (m, 2H), 6.78 (d, 1H), 4.45 (m, 2H), 3.52 (t, 2H).

Analysis for: C$_{27}$H$_{20}$ClH$_5$. Calculated: C, 72.07; H, 4.48; N, 15.57. Found: C, 71.18; H, 4.92; N, 15.63.

EXAMPLE 5

7-Chloro-N-(4-fluorophenyl)-2-phenyl-2H-pyrazolo[4,3-c]quinoline-4-ethanamine

A. 7,10-Dichloro-2-(4-fluorophenyl)-1,2,3,4-tetrahydrobenzo[b][1,6]naphthyridine To a slurry of 13.32 g (0.0776 mol) of 2-amino-4-chlorobenzoic acid and 50 ml of phosphorous oxychloride is added slowly 15 g (0.776 mol) of 1-(p-fluorophenyl)-4-piperidone. The mixture is stirred under reflux for 3 hours. The solution is concentrated in vacuo, dissolved in CHCl$_3$, and added to an ice-NH$_4$OH mixture. The mixture is stirred for ½ hour and extracted with chloroform. The combined extracts are washed with brine, dried over Na$_2$SO$_4$, and concentrated in vacuo to yield 34.36 g of solid. Purification of HPLC affords 3.97 g (15%) of title compound as a brown solid: m.p. 161°–164° C. (dec.); IR (KBr) 1604, 1510, and 1225 cm$^{-1}$; NMR (CDCl$_3$) δ 8.16 (d, 1H), 8.06 (s, 1H), 7.55 (m, 1H), 7.05 (d, 4H), 4.54 (s, 2H), 3.66 (t, 2H), 3.34 (t, 2H).

Analysis for: C$_{18}$H$_{13}$Cl$_2$FN$_2$. Calculated: C, 62.26; H, 3.77; N, 8.07. Found: C, 62.07; H, 3.93; N, 8.02.

B. 7-Chloro-N-(4-fluorophenyl)-2-phenyl-2H-pyrazolo[4,3-c]quinoline-4-ethanamine A solution of 3.5 g (0.01 mol) the compound of step A. above, 2 ml (2.2 g/0.0203 mol) of phenylhydrazine, 1.6 ml of conc. hydrochloric acid, and 100 ml of absolute ethanol is stirred at reflux temperature for 7 hours. On cooling, the resulting precipitate is collected, then dissolved in methanol. Treatment of this solution with Na$_2$CO$_3$ solution results in the formation of a precipitate. The solid is collected to afford 1.7 g (41%) of title compound as tan crystals: IR (KBr) 1610 and 1590 cm$^{-1}$; NMR (DMSO-d$_6$) δ 9.58 (s, 1H), 8.48 (d, 1H), 8.20 (d, 2H), 8.09 (d, 1H), 7.74–7.66 (m, 3H), 7.58–7.52 (m, 1H), 7.0–6.92 (m, 2H), 6.72–6.64 (m, 2H), 5.72 (t, 1H, exchangeable), 3.7–3.62 (m, 2H), and 3.44 (t, 2H).

Analysis for: C$_{24}$H$_{18}$N$_4$ClF. Calculated: C, 69.15; H, 4.35; N, 13.44. Found: C, 68.84; H, 4.36; N, 13.35.

EXAMPLE 6

7-Chloro-2-phenyl-N-(2-pyrazinyl)-2H-pyrazolo-[4,3-c]quinoline-4-ethanamine, hemihydrate

A. 1-[2-Pyrazinyl]-4-piperidinone

A mixture of 20 g (0.1746 mol) of chloropyrazine, 36 g (0.260 mol) of K$_2$CO$_3$, 76 g (0.5308 mol) of 1,4-dioxa-8-azaspiro[4.5]decane, and 80 ml of dimethylformamide is stirred at 100° C. for 3 days. The reaction mixture is cooled, diluted with water, and extracted with ethyl acetate. The combined extracts are washed with water, dried over Na$_2$SO$_4$ and concentrated in vacuo. The residue, 400 ml of 10% sulfuric acid solution and 100 ml of tetrahydrofuran are stirred at ambient temperature for 4 days, diluted with water, basified (NaOH) and extracted with methylene chloride. The extracts are washed with brine, dried over Na$_2$SO$_4$, and concentrated in vacuo. Trituration with ether gives 8.4 g of title compound: IR (KBr) 1720 and 1580 cm$^{-1}$; NMR (CDCl$_3$) δ 8.24–7.88 (m, 3H), 3.98 (t, 4H), and 2.56 (t, 4H).

B. 7,10-Dichloro-1,2,3,4-tetrahydro-2-(2-pyrazinyl)benzo[b][1,6]naphthyridine To a slurry of 20.24 g (0.118 mol) of 2-amino-4-chlorobenzoic acid and 100 ml of POCl$_3$ is added slowly 20.9 g (0.118 mol) of the compound of step A. above. The mixture is stirred under reflux for 3 hrs. and concentrated in vacuo. The residue is dissolved in chloroform, poured into an ice-NH$_4$OH mixture, and stirred for 30 min. The mixture is extracted with chloroform. The combined extracts are washed with brine, dried over Na$_2$SO$_4$, and concentrated in vacuo to yield 40 g of solid. Purification by HPLC affords 3.1 g (8%) of title compound as a white solid: m.p. 182°–184° C. (dec.); IR (KBr) 1612, 1574, and 1479 cm$^{-1}$; NMR (CDCl$_3$) δ 8.37 (s, 1H), 8.20 (m, 2H), 8.08 (s, 1H), 7.98 (s, 1H), 7.59 (m, 1H), 5.02 (s, 2H), 4.11 (t, 2H), 3.37 (t, 2H).

Analysis for: C$_{16}$H$_{12}$Cl$_2$N$_4$. Calculated: C, 58.02; H, 3.65; N, 16.92. Found: C, 57.93; H, 3.73; N, 16.50.

C.

7-Chloro-2-phenyl-N-(2-pyrazinyl)-2H-pyrazolo[4,3-c]quinoline-4-ethanamine, hemihydrate A mixture of 1.5 g (4.53 mmol) of the compound of step B. above, 0.98 mol (9.96 mmol) of phenylhydrazine, 0.75 ml of conc. hydrochloric acid, and 30 ml of absolute ethanol is stirred under reflux for 6 hrs. The cooled precipitate is dissolved in methanol and treated with a $Na_2CO_3$ solution. The precipitate which forms is collected, washed with water, and dissolved in hot benzene-hexanes. On cooling the solid is collected. The filtrate, on standing forms a precipitate which is collected and purified by HPLC to furnish 0.788 g (43%) of title compound: m.p. 201°–203° C. (dec.); IR (KBr) 3250, 1585, and 1510 cm$^{-1}$; NMR (DMSO-$d_6$) δ 9.78 (s, 1H), 8.46 (d, 1H), 8.18 (d, 2H), 8.06 (s, 1H), 7.97 (s, 2H), 7.67 (m, 4H), 7.54 (m, 1H), 7.25 (m, 1H), 3.93 (m, 2H), 3.44 (t, 2H).

Analysis for: $C_{22}H_{17}ClN_6 \cdot \frac{1}{2}H_2O$. Calculated: C, 64.47; H, 4.42; N, 20.51. Found: C, 64.18; H, 4.37; N, 19.78.

EXAMPLE 7

4-[[2-(2-phenyl-2H-pyrazolo[4,3-c]quinolin-4-yl)ethyl]amino]benzoic acid ethyl ester

A.

4-(10-chloro-3,4-dihydrobenzo[b][1,6]-naphthyridin-2(1H)-yl)benzoic acid ethyl ester To a slurry of 0.796 g (5.8 mmol) of 2-aminobenzoic acid and 20 ml of $POCl_3$ is added slowly 1.435 g (5.8 mmol) of 4-(4-oxo-1-piperidinyl)benzonitrile as prepared in Example 1, steps A and B. The mixture is stirred under reflux for 3 hrs. The solution is concentrated in vacuo, dissolved in chloroform, and added to an ice-$NH_4OH$ mixture. The mixture is stirred for ½ hr. and extracted with chloroform. The combined extracts are washed with brine, dried over $NA_2SO_4$, and concentrated in vacuo to yield 3.19 g of solid. Purification by HPLC affords 0.30 g (14%) of title compound as a solid: m.p. 130°–133° C.; IR (KBr) 1705 and 1610 cm$^{-1}$; NMR (DCDl$_3$) δ 8.27 (d, 1H), 8.07 (m, 3H), 7.79 (m, 1H), 7.66 (m, 1H), 7.05 (d, 2H), 4.79 (s, 2H), 4.37 (q, 2H), 3.89 (t, 2H), 3.40 (t, 2H), 1.39 (t, 3H).

Analysis for: $C_{21}H_{19}ClN_2O_2$. Calculated: C, 68.75; H, 5.22; N, 7.64. Found: C, 68.33; H, 5.20; N, 7.67.

B.

4-[[2-(2-phenyl-2H-pyrazolo[4,3-c]quinolin-4-yl)ethyl]amino]benzoic acid ethyl ester A mixture of 0.220 g (0.6 mmol) of the compound of step A. above, 0.13 ml (1.32 mmol) of phenylhydrazine, 0.17 ml of concentrated hydrochloric acid, and 15 ml of absolute ethanol is stirred under reflux for 6 hours. The cooled precipitate is dissolved in methanol and treated with a $Na_2CO_3$ solution. The precipitate which forms is collected and washed with water to yield 0.240 g of tan solid. HPLC gives 64.1 mg, from which, after trituration with ether, 42 mg (1.6%) of title compound is obtained as a solid: m.p. 146°–147° C.; IR (KBr) 3340, 1675, 1600, and 1270 cm$^{-1}$; NMR (DMSO-$d_6$) δ 9.54 (s, 1H), 8.50–7.50 (m, 11H), 6.74–6.64 (m, 3H, 1H exchangeable), 4.24 (q, 2H), 3.82–3.72 (m, 2H), 3.46 (t, 2H), and 1.26 (t, 3H).

Analysis for: $C_{27}H_{24}N_4O_2$. Calculated: C, 74.29; H, 5.54; N, 12.84. Found: C, 73.76; H, 5.51; N, 12.24.

EXAMPLE 8

N-[2-(7-chloro-2-phenyl-2H-pyrazolo[4,3-c]quinolin-4-yl)ethyl]-N-(4-cyanophenyl)-N'-phenylurea A solution of 100 mg (0.24 mmol) of the compound of Example 1, 150 mg (1.26 mmol) of phenylisocyanate, and 8 ml of methylene chloride is stirred at ambient temperature for four days. The resulting precipitate is collected and triturated with ether to afford 88 mg (68%) of title compound: IR (KBr) 3440, 2240, 1670, 1605, 1520, 1510, and 1440 cm$^{-1}$; NMR (DMSO-$d_6$) δ 9.56 (s, 1H), 8.72 (s, 1H, exchangeable), 8.48–6.96 (complex m, 17H), 4.46 (t, 2H), and 3.5 (t, 2H).

Analysis for: $C_{32}H_{23}N_6OCl$. Calculated: C, 70.78; H, 4.27; N, 15.48. Found: C, 70.35; H, 4.42; N, 15.5.

EXAMPLE 9

4-[[2-(7-chloro-2-phenyl-2H-pyrazolo[4,3-c]-quinolin-4-yl)ethyl](phenylamino)carbonyl]amino]benzoic acid ethyl ester A solution of 95 mg (0.2 mmol) of the compound of Example 2, 150 mg (1.26 mmol) of phenylisocyanate, and 5 ml of methylene chloride is heated to reflux for 5 minutes then stirred at ambient temperature for four days. The reaction mixture is concentrated in vacuo. The residue is triturated with ether to provide 47 mg (40%) of title compound: IR (KBr) 3260 (br), 1710, 1670, 1595, 1500, and 1440 cm$^{-1}$; NMR (DMSO-$d_6$) δ 9.52 (s, 1H), 8.56 (s, 1H, exchangeable), 8.46–6.92 (complex m, 17H), 4.45 (t, 2H), 4.34 (q, 2H), 3.50 (t, 2H), and 1.32 (t, 3H).

Analysis for: $C_{34}H_{28}N_5O_3Cl_3$. Calculated: C, 69.20; H, 4.78; N, 11.87. Found: C, 68.78; H, 4.87; N, 11.44.

EXAMPLE 10

N'-(4-Chlorophenyl)-N-[2-(7-chloro-2-phenyl-2H-pyrazolo[4,3-c]quinolin-4-yl)ethyl]-N-(4-cyanophenyl)urea A mixture of 150 mg (0.35 mmol) of the compound of Example 1, 100 mg (0.65 mmol) of p-chlorophenylisocyanate, and 10 ml of methylene chloride is stirred at ambient temperature overnight. The resulting precipitate is collected to furnish 121 mg (60%) of title compound: IR (KBr) 3360, 2220, 1660, 1590, 1520, 1500, 1490 cm$^{-1}$; NMR (DMSO-$d_6$) δ 9.56 (s, 1H), 8.8 (s, 1H, exchangeable), 8.8–7.26 (complex m, 16H), 4.45 (t, 2H), and 3.5 (t, 2H).

Analysis for: $C_{32}H_{22}N_6OCl_2$. Calculated: C, 66.55; H, 3.84; N, 14.56. Found: C, 66.56; H, 3.87; N, 14.35.

EXAMPLE 11

4-[[[(4-chlorophenyl)amino]carbonyl][2-(7-chloro-2-phenyl-2H-pyrazolo[4,3-c]quinolin-4-yl)ethyl]amino]benzoic acid ethyl ester, hydrate A solution of 95 mg (0.2 mmol) of the compound of Example 2, 100 mg (0.65 mmol) of p-chlorophenylisocyanate, and 5 ml of methylene chloride is heated to reflux for 5 minutes, then stirred at ambient temperature for four days. The reaction mixture is concentrated in vacuo. The residue is triturated with ether to give 84 mg (67%) of title compound: IR (KBr) 3280, 1710, 1665, 1590, and 1490 cm$^{-1}$; NMR (DMSO-$d_6$) δ 9.52 (s, 1H), 8.64 (s, 1H, exchangeable), 8.44–7.24 (complex-m, 16H), 4.42 (t, 2H), 4.33 (q, 2H), 3.48 (t, 2H), and 1.32 (t, 3H)

Analysis for: $C_{34}H_{27}N_5O_3Cl_2 \cdot H_2O$. Calculated: C, 63.55; H, 4.55; N, 10.90. Found: C, 63.17; H, 4.33; N, 10.55.

EXAMPLE 12

7-Chloro-N-[(4-methylsulfonyl)phenyl]-2-phenyl-2H-pyrazolo[4,3-c]quinoline-4-ethanamine

A.
8-[4-(Methylsulfonyl)phenyl]-1,4-dioxa-8-azaspiro[4.5]-decane

A mixture of 10 g (0.057 mol) of p-fluorophenyl methyl sulfone, 8.72 g (0.063 mol) of $K_2CO_3$, 24.66 g (0.172 mol) of 1,4-dioxa-8-azaspiro[4.5]decane, and 50 ml of acetonitrile is stirred overnight at 90°–100° C. After cooling, the mixture is diluted with water and extracted with methylene chloride. The combined extracts are washed with brine, dried over $Na_2SO_4$, and concentrated in vacuo. Trituration with ether affords 13.11 g (77%) of title compound as a white solid: m.p. 192°–194° C.; IR (KBr) 1588, 1369, and 1290 cm$^{-1}$; NMR (CDCl$_3$) δ 7.74 (m, 2H), 6.96 (m, 2H), 4.02 (s, 4H), 3.54 (m, 4H), 3.03 (s, 3H), 1.81 (m, 4H).

Analysis for: $C_{14}H_{19}NO_4S$. Calculated: C, 56.54; H, 6.44; N, 4.71. Found: C, 56.37; H, 6.55; N, 4.97.

B. 1-[4-(Methylsulfonyl)phenyl]-4-piperidinone

A mixture of 12.97 g (0.0436 mol) of the ketal of A, above, and 200 ml of 10% sulfuric acid/tetrahydrofuran (2:1) solution is stirred at 60°–70° C. for 4 hours and is then allowed to stand at room temperature for 3 days. The mixture is diluted with water and extracted with methylene chloride. The combined extracts are washed with brine, dried over $Na_2SO_4$, and concentrated in vacuo. Trituration with ether gives 10.07 g (91.1%) of title compound as a white solid: m.p. 183°–185° C.; IR (KBr) 3410, 1710, 1585, and 1160 cm$^{-1}$; NMR (CDCl$_3$) δ 7.79 (d, 2H), 6.98 (d, 2H), 3.79 (t, 4H), 3.04 (s, 3H), 2.61 (t, 4H).

Analysis for: $C_{12}H_{15}NO_3S$. Calculated: C, 56.89; H, 5.97; N, 5.53. Found: C, 57.36; H, 6.23; N, 5.88.

C.
7,10-Dichloro-1,2,3,4-tetrahydro-2-(4-methylsulfonyl)-phenylbenzo[b][1,6]naphthyridine To a slurry of 6.46 g (0.0376 mol) of 2-amino-4-chlorobenzoic acid and 35 ml of phosphorous oxychloride is added portionwise 9.53 g (0.0376 mol) of the compound of B, above. The mixture is stirred under reflux for 2 hours and concentrated in vacuo. The residue is dissolved in chloroform and slowly added to an ice-NH$_4$OH mixture. The mixture is stirred for 30 minutes before being extracted with chloroform. The combined extracts are washed with brine, dried over Na$_2$SO$_4$, and concentrated in vacuo to yield 9.92 g of solid. Purification by HPLC and trituration with ether furnishes 1.7 g (11%) of title compound as a light brown solid: m.p. 195°–198° C. (dec.); IR (KBr) 1592, 1296, and 1135 cm$^{-1}$; NMR (CDCl$_3$) δ 8.18 (d, 1H), 8.07 (s, 1H), 7.86 (d, 2H), 7.59 (m, 1H), 7.09 (d, 2H), 4.78 (s, 2H), 3.89 (t, 2H), 3.37 (t, 2H), 3.02 (s, 3H).

Analysis for: $C_{19}H_{16}Cl_2N_2O_2S$. Calculated: C, 56.02; H, 3.96; N, 6.88. Found: C, 56.32; H, 3.97; N, 7.14.

D.
7-Chloro-N-[(4-methylsulfonyl)phenyl]-2-phenyl-2H-pyrazolo[4,3-c]quinoline-4-ethanamine A solution of 1.0 g (2.45 mmole) of the compound of C, above, 0.69 ml (0.75/6.98 mmole) of phenylhydrazine, 0.74 ml of concentrated hydrochloric acid, and 120 ml of absolute ethanol is stirred at reflux temperature for 7 hours. On cooling, the resulting precipitate is collected, then dissolved in methanol. Treatment of this solution with Na$_2$CO$_3$ solution results in the formation of a precipitate. Recrystallization from acetonitrile affords 685 mg (59%) of lemon-colored crystals, m.p. 217°–218° C.; IR (KBr) 3300, 1590, 1500, 1300 and 1130 cm$^{-1}$; NMR (DMSO-d$_6$) δ 9.58 (s, 1H), 8.48 (d, 1H), 8.18 (m, 2H), 7.76–7.5 (m, 7H), 6.86 (t, 1H, exchangeable), 6.81 (d, 1H), 3.80 (m, 2H), 3.48 (t, 2H), and 3.08 (s, 3H).

Analysis for: $C_{25}H_{21}ClN_4O_2S$. Calculated: C, 62.95; H, 4.44; N, 11.75. Found: C, 62.68; H, 4.49; N, 11.91.

EXAMPLE 13

6-[[2-(7-Chloro-2-phenyl-2H-pyrazolo[4,3-c]quinolin-4-yl)ethyl]amino]-3-pyridinecarbonitrile

A.
6-(1,4-Dioxa-8-azaspiro[4.5]decan-8-yl)-3-pyridinecarbonitrile, ¼ hydrate A mixture of 14 g (0.101 mol) 6-chloronicotinonitrile, 43 g (0.30 mol) of 1,4-dioxa-8-azaspiro[4.5]decane, 22 g (0.159 mol) of K$_2$CO$_3$, and 100 ml of acetonitrile is stirred at 90°–100° C. for four days. The reaction mixture is allowed to cool to ambient temperature, diluted with water and extracted with methylene chloride. The combined extracts are washed with brine, dried over Na$_2$SO$_4$, and concentrated in vacuo to give a pasty solid. Trituration with ether furnishes 24.3 g (98%) of title compound: IR (KBr) 2200, 1590, and 1490 cm$^{-1}$; NMR (CDCl$_3$) δ 8.4 (m, 1H), 7.6 (m, 1H), 6.63 (m, 1H), 4.0 (s, 4H), 3.8 (m, 4H), and 1.75 (m, 4H).

Analysis for: $C_{13}H_{15}N_3O_2 \cdot \frac{1}{4}H_2O$. Calculated: C, 62.50; H, 6.26; N, 16.82. Found: C, 62.73; H, 6.06; N, 16.65.

B. 6-(4-Oxo-1-piperidinyl)-3-pyridinecarbonitrile

A mixture of 23 g (0.0942 mol) of the ketal of A, above, 500 ml of 10% sulfuric acid solution, and 250 ml of tetrahydrofuran is stirred at ambient temperature for 5 days. The reaction mixture is diluted with water and extracted with methylene chloride. The combined organic extracts are dried over Na$_2$SO$_4$ and concentrated in vacuo to give a pasty solid. Trituration with ether provides 14.2 g (75%) of title compound: IR (KBr) 2200, 1710, 1600 and 1500 cm$^{-1}$; NMR (CDCl$_3$) δ 8.45 (m, 1H), 7.67 (m, 1H), 6.7 (m, 1H), 4.03 (t, 4H) and 2.57 (t, 4H).

Analysis for: $C_{11}H_{11}N_3O$. Calculated: C, 65.66; H, 5.51; N, 20.88. Found: C, 65.34; H, 5.59; N, 20.60.

C.
6-(7,10-Dichloro-3,4-dihydrobenzo[b][1,6]naphthyridin-2(1H)-yl)-3-pyridinecarbonitrile, hemihydrate To a slurry of 11.5 g (0.067 mol) of 2-amino-4-chlorobenzoic acid and 120 ml of phosphorous oxychloride is added portionwise 13.5 g (0.067 mol) of the compound of B, above. The mixture is stirred under reflux for 3 hours and concentrated in vacuo. The residue is taken up in chloroform and poured carefully into a mixture of ice-NH$_4$OH and stirred for 30 minutes before extraction with chloroform. The combined extracts are washed with brine, dried over Na$_2$SO$_4$, and concentrated in vacuo. The resultant solid is triturated in ether and dried under vacuum to yield 19.9 g of title compound; m.p. 171°-173° C. (yield 84%). IR (KBr) 2205, 1600, 1540, 1500 and 1420 cm$^{-1}$; NMR (DMSO-d$_6$) δ 8.50-7.40 (complex-m, 5H), 6.77 (d, 1H), 5.05 (s, 2H), 4.10 (t, 2H), and 3.30 (t, 2H).

Analysis for: $C_{18}H_{12}Cl_2N_4 \cdot \frac{1}{2}H_2O$. Calculated: C, 59.35; H, 3.60; N, 15.38. Found: C, 59.50; H, 3.66; N, 15.31.

D.
6-[[2-(7-Chloro-2-phenyl-2H-pyrazolo[4,3-c]quinolin-4-yl)ethyl]amino]-3-pyridinecarbonitrile A mixture of 6.0 g (17.0 mmol) of the compound of C, above, 4.7 ml (48.0 mmol) of phenylhydrazine, 5.1 ml of concentrated hydrochloric acid and 350 ml of absolute ethanol is stirred under reflux for 6 hours. The cooled precipitate is dissolved in methanol and treated with Na$_2$CO$_3$ solution. The precipitate which forms is collected and washed with water to give a solid. Recrystallization from toluene affords 0.779 g (11%) of the title compound: m.p. 207°-208° C. IR (KBr) 2820, 2200, 1600 and 1510 cm$^{-1}$; NMR (DMSO-d$_6$) δ 9.56 (s, 1H), 8.48 (d, 2H), 8.19 (d, 2H), 8.08 (d, 1H), 7.8 (t, 1H, exchangeable), 7.72 (m, 4H), 7.57 (t, 1H), 6.62 (d, 1H), 4.02 (m, 2H), and 3.46 (t, 2H).

Analysis for: $C_{24}H_{17}ClN_6$. Calculated: C, 67.84; H, 4.03; N, 19.78. Found: C, 67.38; H, 4.30; N, 19.89.

EXAMPLE 14

The ability of the compounds of the inventions to inhibit interleukin 1 is measured by the ability of the test compounds to inhibit the IL 1-induced release of neutral protease from rabbit articular chondrocytes.

This assay is carried out as follows:

Isolation of rabbit chondrocytes:

Male New Zealand White rabbits are anesthetized with 50 mg/kg of ketamine (i.m.) and killed by an intracardiac injection of 3 mls. of Nembutal. The knee joints of both legs are resected and the articular surfaces are exposed. Cartilage slices are obtained using a scalpel and are placed in a tissue culture dish (100 mm diameter) containing 10 mls of Hank's balanced salt solution (HBSS). The chondrocytes within the cartilage slices are then liberated by a series of enzyme digestions. The slices are incubated for 10 min. at 37° C. in 0.05% hyaluronidase (Sigma H-3884), rinsed with HBSS and incubated with 0.2% trypsin (Sigma T-2395) for 10 min. at 37° C. The slices are rinsed again and incubated for 10 mins. at 37° C. with 1.2% collagenase (Sigma C-5138). The slices are then rinsed again with HBSS and resuspended in 10 ml of Ham's F-12 medium containing 10% fetal bovine calf serum (FCS) and 0.2% collagenase and incubated overnight at 37° C. in a 5% CO$_2$ incubator. The next day, the medium containing the digested cartilage fragments and liberated chondrocytes is transferred to a 15 ml centrifuge tube and the cells are collected by centrifugation and washed twice and resuspended in Ham's F-12 medium. The cells are then plated into 24-well tissue culture plates (2×10$^5$ cells/well) and incubated at 37° C. until confluent (usually 4–6 days).

Stimulation of chondrocytes and drug treatment:

The confluent chondrocytes are rinsed twice with serum-free Ham's F-12 medium and 1 ml is added to each well. Fifty μl of purified human IL 1 (100 Units/ml; Genzyme Corporation, Boston, MA) is then added to stimulate these cells to secrete neutral protease. To measure drug effects, the cells are treated with test compound 10 min. prior to addition of IL 1. The standard screening dose is 10 μM. Twenty-four hours after IL 1 stimulation, supernatant fluids are collected and assayed for neutral protease activity.

Neutral protease assay:

The neutral protease activity of chondrocyte supernatant fluids is determined by their ability to degrade an insoluble protease substrate, azocoll (Sigma). Supernatants are treated for 10 min. at room temperature with 350 μM p-aminophenylmurcuric acetate to activate the latent enzyme. Three hundred μl of supernatant is then mixed with 500 μl of a 20 mg/ml suspension of azocoll and incubated at 37° C. for 18-24 hrs. with gentle rocking. The mixtures are centrifuged and the amount of substrate hydrolyzed is determined by measuring the absorbance of the supernatant at 520 nm.

Drug effects are calculated as the % change in enzyme activity (absorbance) by supernatants from drug-treated chondrocytes relative to enzyme activity of supernatants from vehicle-treated chondrocytes as follows:

% Inhibition of Protease Secretion =

$$\frac{(A_{520}) \text{ Untreated Supernatant} - A_{520} \text{ Drug treated Supernatent}}{A_{520} \text{ Untreated Supernatant}} (\times\ 100)$$

Where tested in this assay, the compounds of the invention gave the following results:

| Compound of Example No. | Dose (μM) | % Inhibition (I.S.D.) |
|---|---|---|
| 1 | 10 | 88 ± 2 |
|   | 1 | 75 ± 5 |
|   | 0.1 | 60 ± 13 |
| 2 | 10 | 85 ± 3 |
|   | 1 | 70 ± 4 |
|   | 0.1 | 41 ± 10 |
| 3 | 10 | 79 ± 29 |
|   | 1 | 22 |
| 4 | 10 | ≦20 |
| 5 | 10 | 14 |
| 6 | 10 | 60 |
| 7 | 10 | 83 |
| 8 | 10 | ≦20 |
| 9 | 10 | 49 |
| 10 | 10 | 51 |
| 11 | 10 | 47 |
| 12 | 10 | 41 |

The results show that the compounds tested exhibit a moderate to very significant inhibition of IL 1-induced protease secretion.

EXAMPLE 15

The compounds of the invention are tested in the rat carrageenan paw edema assay to determine their ability to inhibit the acute inflammatory response.

This assay is carried out as follows:

140–180 gm male Sprague-Dawley rats, in groups of 6 animals, are injected subcutaneously in the right paw with 0.1 ml of 1% carrageenan at zero time. Mercury plethysmographic readings (ml) of the paw are made at zero time and 3 hours later. Test compounds are suspended or dissolved in 0.5% methylcellulose and given perorally 1 hour prior to carrageenan administration.

The increase in paw volume (edema in ml.) produced by the carrageenan is measured. Paw edema is calculated (3 hour volume minus zero time volume), and percent inhibition of edema is determined. Unpaired Student's t-test is used to determine statistical significance.

The activity of standard drugs in this assay is as follows:

| Drug | Oral ED$_{50}$ (95% C.L.) mg/kg |
| --- | --- |
| Indomethacin | 3.7 (0.6, 23.8) |
| Aspirin | 145.4 (33.1, 645.6) |
| Phenylbutazone | 26.2 (2.3, 291.0) |

When tested in this assay, the compounds of the invention gave the following results:

| Compound of Example No. | % Inhibition at 50 mg/kg (peroral) |
| --- | --- |
| 1 | 38 |
| 2 | 32 |

The results show that the compounds tested have activity in the rat carrageenan paw edema assay, evidencing an effect on the acute inflammatory response.

What is claimed is:

1. A compound having the formula

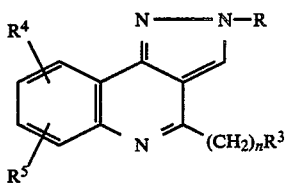

wherein

R is, phenyl, naphthyl, pyrid(-2-, 3- or 4-)yl, quinolin(-2-, -3- or -4-)yl or phenyl, naphthyl, pyrid(-2-, -3- or -4-)yl or quinolin(-2-, -3- or -4-)yl substituted by halo, lower alkyl, lower alkoxy, nitro, cyano, amino, monolower alkyl amino, di-lower alkyl amino, carboxy, lower alkoxycarbonyl or hydroxy;

$R^1$ is phenyl, phenyl lower alkyl, naphthyl, pyrid(-2-, -3- or -4-)yl, quinolin(-2-, -3-, -4-)yl, pyrazin(-2- or -3-)yl, pyrimidin(-2-, -4- or -5-)yl, pyridazin(-3, -4- or -5-)yl, quinoxalin(-2- or -3-)yl or quinazolin(-2- or -4-)yl or any of the foregoing substituted with halo, lower alkyl, carboxy, cyano, nitro, lower alkylsulfonyl, lower alkoxy carbonyl or lower alkyl substituted by fluoro, carboxy, cyano, nitro or lower alkoxy carbonyl;

$R^2$ is hydrogen, lower alkyl, phenyl or benzyl;

$R^3$ is $NR^2R^1$ or $NR^6R^1$;

$R^4$ and $R^5$ are each independently, hydrogen, halo, lower alkoxy, lower alkyl, trifluoromethyl, cyano, nitro, carboxy or lower alkoxycarbonyl;

$R^6$ is carbamoyl, phenylcarbamoyl, or halophenylcarbamoyl; and n is 1—5.

2. The compound of claim 1, having the name 4-[[2-(7-chloro-2-phenyl-2H-pyrazolo[4,3-c]quinolin-4-yl)ethyl]amino]benzonitrile.

3. The compound of claim 1, having the name 4-[[2-(7-chloro-2-phenyl-2H-pyrazolo[4,3-c]quinolin-4-yl)ethyl]amino]benzoic acid ethyl ester.

4. The compound of claim 1, having the name 7-chloro-2-phenyl-N-(2-pyrimidinyl)-2H-pyrazolo[4,3-c]quinoline-4-ethanamine.

5. The compound of claim 1, having the name 7-chloro-2-phenyl-N-(2-quinolinyl)-2H-pyrazolo[4,3-c]quinoline-4-ethanamine.

6. The compound of claim 1, having the name 7-chloro-N-(4-fluorophenyl)-2-phenyl-2H-pyrazolo[4,3-c]quinoline-4-ethanamine.

7. The compound of claim 1, having the name 7-chloro-2-phenyl-N-(2-pyrazinyl)-2H-pyrazolo[4,3-c]quinoline-4-ethanamine.

8. The compound of claim 1, having the name 4-[[2-(2-phenyl-2H-pyrazolo[4,3-c]quinolin-4-yl)ethyl]amino]benzoic acid ethyl ester.

9. The compound of claim 1, having the name N-[2-(7-chloro-2-phenyl-2H-pyrazolo[4,3-c]quinolin-4-yl)ethyl]-N-(4-cyanophenyl)-N'-phenylurea.

10. The compound of claim 1, having the name 4-[[2-(7-chloro-2-phenyl-2H-pyrazolo[4,3-c]quinolin-4-yl)ethyl](phenylamino)carbonyl]amino]benzoic acid ethyl ester.

11. The compound of claim 1, having the name N'-(4-chlorophenyl)-N-[2-(7-chloro-2-phenyl-2H-pyrazolo[4,3-c]quinolin-4-yl)ethyl]-N-(4-cyanophenyl)urea.

12. The compound of claim 1, having the name 4-[[[(4-chlorophenyl)amino]carbonyl][2-(7-chloro-2-phenyl-2H-pyrazolo[4,3-c]quinolin-4-yl)ethyl]amino]benzoic acid ethyl ester.

13. The compound of claim 1, having the name 7-chloro-N-[(4-methylsulfonyl)phenyl]-2-phenyl-2H-pyrazolo[4,3-c]quinoline-4-ethanamine.

14. The compound of claim 1, having the name 6-[[2-(7-chloro-2-phenyl-2H-pyrazolo[4,3-c]quinolin-4-yl)ethyl]amino]-3-pyridinecarbonitrile.

* * * * *